United States Patent
Hornik

(10) Patent No.: US 6,706,862 B1
(45) Date of Patent: *Mar. 16, 2004

(54) BACKBONE-CYCLIZED BPI PEPTIDOMIMETICS

(75) Inventor: Vered Hornik, Rehovot (IL)

(73) Assignee: Peptor Limited, Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,028

(22) Filed: Apr. 20, 2000

Related U.S. Application Data

(62) Division of application No. 08/569,042, filed on Dec. 7, 1995, now Pat. No. 6,117,974.

(51) Int. Cl.⁷ .................. A61K 38/12; A61K 38/04; A61K 38/00; C07K 16/00; C07K 17/00
(52) U.S. Cl. .................. 530/517; 530/317; 530/328; 514/11; 514/15; 514/16; 930/DIG. 436
(58) Field of Search .................. 435/7.1, 501; 514/11, 514/15, 16; 530/317, 333, 328; 970/DIG. 436

(56) References Cited

U.S. PATENT DOCUMENTS

| | | | | |
|---|---|---|---|---|
| 5,627,153 A | * | 5/1997 | Little, II et al. | 514/12 |
| 5,723,575 A | * | 3/1998 | Gilon et al. | 530/317 |
| 5,770,687 A | * | 6/1998 | Hornik et al. | 530/311 |
| 5,807,979 A | * | 9/1998 | Satterwait, Jr. et al. | 530/317 |
| 5,811,392 A | * | 9/1998 | Gilon et al. | 514/11 |
| 6,051,554 A | * | 4/2000 | Hornik et al. | 514/11 |
| 6,107,275 A | * | 8/2000 | Harbeson et al. | 514/11 |
| 6,117,974 A | * | 9/2000 | Gilon et al. | 530/317 |

FOREIGN PATENT DOCUMENTS

WO  0 564 739 A2 * 10/1993

* cited by examiner

*Primary Examiner*—Andrew Wang
*Assistant Examiner*—Tomas Friend
(74) *Attorney, Agent, or Firm*—Winston & Strawn LLP

(57) ABSTRACT

Novel backbone-cyclized BPI peptide analogs and methods of making the same by the use of bridging groups attached via the alpha nitrogens of amino acid derivatives to provide novel non-peptidic linkages. Novel building units used in the synthesis of these backbone-cyclized peptide analogs are $N^{\alpha}$-functionalized amino acids constructed to include a spacer and a terminal functional group. The reactive terminal functional groups are protected by specific protecting groups that can be selectively removed to effect either backbone-to-backbone or backbone-to-side chain cyclizations. A plurality of these $N\alpha\omega$-functionalized amino acids are incorporated into a library of peptide sequences, preferably during solid phase peptide synthesis.

14 Claims, No Drawings

SEQUENCE LISTING

<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa = Any Amino Acid

<400> SEQUENCE: 1

Lys Trp Leu Ile Gln Leu Phe His Lys Lys
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 5 = GlyC2
<220> FEATURE:
<221> NAME/KEY: VARIANT
<222> LOCATION: (1)...(10)
<223> OTHER INFORMATION: Xaa at Position 9 = GlyN2

<400> SEQUENCE: 2

Lys Trp Leu Ile Xaa Leu Phe His Xaa Lys
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 5 = GlyC2
<220> FEATURE:
<221> NAME/KEY: VARIANT
<222> LOCATION: (1)...(10)
<223> OTHER INFORMATION: Xaa at Position 8 = GlyN2

<400> SEQUENCE: 3

Lys Trp Leu Ile Xaa Leu Phe Xaa Lys Lys
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 5 = GlyC2
<220> FEATURE:
<221> NAME/KEY: VARIANT
<222> LOCATION: (1)...(10)
<223> OTHER INFORMATION: Xaa at Position 7 = GlyN2

<400> SEQUENCE: 4

Lys Trp Leu Ile Xaa Leu Xaa His Lys Lys
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 5 = GlyC2
<220> FEATURE:
<221> NAME/KEY: VARIANT
<222> LOCATION: (1)...(10)
<223> OTHER INFORMATION: Xaa at Position 6 = GlyN2

```
<400> SEQUENCE: 5

Lys Trp Leu Ile Xaa Xaa Phe His Lys Lys
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 4 = GlyC2
<220> FEATURE:
<221> NAME/KEY: VARIANT
<222> LOCATION: (1)...(10)
<223> OTHER INFORMATION: Xaa at Position 9 = GlyN2

<400> SEQUENCE: 6

Lys Trp Leu Xaa Gln Leu Phe His Xaa Lys
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 4 = GlyC2
<220> FEATURE:
<221> NAME/KEY: VARIANT
<222> LOCATION: (1)...(10)
<223> OTHER INFORMATION: Xaa at Position 8 = GlyN2

<400> SEQUENCE: 7

Lys Trp Leu Xaa Gln Leu Phe Xaa Lys Lys
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 4 = GlyC2
<220> FEATURE:
<221> NAME/KEY: VARIANT
<222> LOCATION: (1)...(10)
<223> OTHER INFORMATION: Xaa at Position 7 = GlyN2

<400> SEQUENCE: 8

Lys Trp Leu Xaa Gln Leu Xaa His Lys Lys
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 4 = GlyC2
```

```
<220> FEATURE:
<221> NAME/KEY: VARIANT
<222> LOCATION: (1)...(10)
<223> OTHER INFORMATION: Xaa at Position 6 = GlyN2

<400> SEQUENCE: 9

Lys Trp Leu Xaa Gln Xaa Phe His Lys Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 3 = GlyC2
<220> FEATURE:
<221> NAME/KEY: VARIANT
<222> LOCATION: (1)...(10)
<223> OTHER INFORMATION: Xaa at Position 9 = GlyN2

<400> SEQUENCE: 10

Lys Trp Xaa Ile Gln Leu Phe His Xaa Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 3 = GlyC2
<220> FEATURE:
<221> NAME/KEY: VARIANT
<222> LOCATION: (1)...(10)
<223> OTHER INFORMATION: Xaa at Position 8 = GlyN2

<400> SEQUENCE: 11

Lys Trp Xaa Ile Gln Leu Phe Xaa Lys Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 3 = GlyC2
<220> FEATURE:
<221> NAME/KEY: VARIANT
<222> LOCATION: (1)...(10)
<223> OTHER INFORMATION: Xaa at Position 7 = GlyN2

<400> SEQUENCE: 12

Lys Trp Xaa Ile Gln Leu Xaa His Lys Lys
1               5                   10

<210> SEQ ID NO 13
<211> LENGTH: 10
<212> TYPE: PRT
<213> ORGANISM: Artificial Sequence
<220> FEATURE:
```

```
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 3 = GlyC2
<220> FEATURE:
<221> NAME/KEY: VARIANT
<222> LOCATION: (1)...(10)
<223> OTHER INFORMATION: Xaa at Position 6 = GlyN2

<400> SEQUENCE: 13

Lys Trp Xaa Ile Gln Xaa Phe His Lys Lys
 1               5                   10

<210> SEQ ID NO 14
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 2 = GlyC2
<220> FEATURE:
<221> NAME/KEY: VARIANT
<222> LOCATION: (1)...(10)
<223> OTHER INFORMATION: Xaa at Position 9 = GlyN2

<400> SEQUENCE: 14

Lys Xaa Leu Ile Gln Leu Phe His Xaa Lys
 1               5                   10

<210> SEQ ID NO 15
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 2 = GlyC2
<220> FEATURE:
<221> NAME/KEY: VARIANT
<222> LOCATION: (1)...(10)
<223> OTHER INFORMATION: Xaa at Position 8 = GlyN2

<400> SEQUENCE: 15

Lys Xaa Leu Ile Gln Leu Phe Xaa Lys Lys
 1               5                   10

<210> SEQ ID NO 16
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 2 = GlyC2
<220> FEATURE:
<221> NAME/KEY: VARIANT
<222> LOCATION: (1)...(10)
<223> OTHER INFORMATION: Xaa at Position 7 = GlyN2

<400> SEQUENCE: 16

Lys Xaa Leu Ile Gln Leu Xaa His Lys Lys
 1               5                   10
```

```
<210> SEQ ID NO 17
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 2 = GlyC2

<400> SEQUENCE: 17

Lys Xaa Leu Ile Gln Leu Phe His Lys Lys
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (1)...(10)
<223> OTHER INFORMATION: Xaa at Position 2 = D1Nal
<220> FEATURE:
<221> NAME/KEY: VARIANT
<222> LOCATION: (1)...(10)
<223> OTHER INFORMATION: Xaa at Position 3 = GlyC2
<220> FEATURE:
<221> NAME/KEY: VARIANT
<222> LOCATION: (1)...(10)
<223> OTHER INFORMATION: Xaa at Position 8 = GlyN2

<400> SEQUENCE: 18

Lys Xaa Xaa Ile Gln Leu Phe Xaa Lys Lys
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: BPI Peptidomimetic
<220> FEATURE:
<221> NAME/KEY: VARIANT
<222> LOCATION: (2)...(2)
<223> OTHER INFORMATION: Xaa = Trp, 2Nal, D2Nal, 1Nal, D1Nal, GlyC1,
     GlyC2, GlyC3, GlyN1, GlyN2, or GlyN3
<220> FEATURE:
<221> NAME/KEY: VARIANT
<222> LOCATION: (3)...(3)
<223> OTHER INFORMATION: Xaa = Leu, GlyC1, GlyC2, GlyC3, GlyN1, GlyN2,
     or GlyN3
<220> FEATURE:
<221> NAME/KEY: VARIANT
<222> LOCATION: (4)...(4)
<223> OTHER INFORMATION: Xaa = absent, Ile, Gly, Ala, GlyC1, GlyC2,
     GlyC3, GlyN1, GlyN2, or GlyN3
<220> FEATURE:
<221> NAME/KEY: VARIANT
<222> LOCATION: (5)...(5)
<223> OTHER INFORMATION: Xaa = Gln, GlyC1, GlyC2, GlyC3, GlyN1, GlyN2,
     or GlyN3
<220> FEATURE:
<221> NAME/KEY: VARIANT
<222> LOCATION: (6)...(6)
<223> OTHER INFORMATION: Xaa = Leu, GlyC1, GlyC2, GlyC3, GlyN1, GlyN2,
     or GlyN3
<220> FEATURE:
<221> NAME/KEY: VARIANT
<222> LOCATION: (7)...(7)
<223> OTHER INFORMATION: Xaa = Phe, DPhe, Phg, PNO2Phe, pFphe, GlyC1,
     GlyC2, GlyC3, GlyN1, GlyN2, or GlyN3
<220> FEATURE:
```

-continued

```
<221> NAME/KEY: VARIANT
<222> LOCATION: (8)...(8)
<223> OTHER INFORMATION: Xaa = His, GlyC1, GlyC2, GlyC3, GlyN1, GlyN2,
      or GlyN3
<220> FEATURE:
<221> NAME/KEY: VARIANT
<222> LOCATION: (9)...(9)
<223> OTHER INFORMATION: Xaa = Lys, GlyC1, GlyC2, GlyC3, GlyN1, GlyN2,
      or GlyN3

<400> SEQUENCE: 19

Lys Xaa Xaa Xaa Xaa Xaa Xaa Xaa Xaa Lys
 1               5                  10
```

BACKBONE-CYCLIZED BPI PEPTIDOMIMETICS

CROSS-REFERENCE TO RELATED APPLICATIONS

This application is a division of U.S. application Ser. No. 08/569,042, filed Dec. 7, 1995, now U.S. Pat. No. 6,117,974 the content of which is expressly incorporated herein by reference thereto.

FIELD OF THE INVENTION

This invention relates to novel conformationally constrained backbone cyclized Bactericidal/Permeability Increasing Protein ("BPI") peptidomimetics, to libraries of the same, to methods for the production of such peptidomimetics libraries and to methods of using such materials to screen for biologically active compounds.

BACKGROUND OF THE INVENTION

Classically, the pharmaceutical industry has screened a wide variety of compounds derived from natural sources to yield potential drug candidates or lead compounds for the development of new drugs. These laborious screening efforts have relied on the random testing of a vast number of chemical entities. In recent years, various strategies have been adopted for the generation of libraries of compounds that are subsequently screened as a novel, rational approach to drug discovery and development.

It has become apparent that a variety of methodologies can be applied to the problem of generating a diverse group of candidate compounds, based on the known principles of peptide chemistry and/or molecular biology. Peptides are a convenient class of molecules for the generation of combinatorial libraries, since they are composed of a finite set of amino acid building units, which can be efficiently assembled either by chemical synthesis or transcription/translation of DNA. Combinatorial libraries are discussed by Gallop et al., *J. Med. Chem.*, 37, 1233–1251 (1994); Gordon et al., *J. Med. Chem.*, 37, 1385–1401 (1994); Pinilla et al., *Biopolymers (Peptide Science)*, 37, 221–240, (1995); and Lebl et al., *Biopolymers (Peptide Science)*, 37, 177–198 (1995). The set of amino acid building units can include only the naturally encoded amino acids, when the libraries are encoded by oligonucleotides on a plasmid, phage, or any other vector. This set can be expanded to include both D and L amino acids and/or non-natural amino acids in synthetic libraries.

Linear peptides suffer from several serious drawbacks as potential drugs, inasmuch as they are notoriously unstable in vivo, often lack high affinity of binding to their receptor, frequently lack selectivity to one kind of receptor, and generally have poor oral bioavailability. In efforts to overcome such problems, it is also possible to utilize the methodologies developed in connection with synthetic peptide libraries to generate collections of cyclic peptides, novel biopolymers and even novel branched oligomeric compounds, reviewed by Zuckermann, *Current Opinion in Structural Biology*, 3, 580–584 (1993).

One of the most significant synthetic technologies that facilitate the generation and screening of diverse chemical libraries is the resin-splitting method, which is a polymer supported multiple synthesis procedure that allows a high degree of control over the composition of a peptide mixture. Mixtures are generated by dividing a solid support into individual portions, and coupling a different amino acid to each portion, and then recombining the portions. These steps may be performed in an iterative fashion to provide the required degree of diversity.

Totally random libraries generated by these types of methods are disclosed in WO92/00091 and WO92/09300. Each individual bead will contain a unique peptide sequence, which can be probed for activity with a soluble receptor or antibody. Positive beads can be isolated and sequenced using Edman sequencing chemistry. WO92/00091 further discloses methods to provide selectively cleavable linkers between peptide and resin, such that part of the peptide can be liberated from the resin and assayed for activity in soluble form, while another part can be sequenced. In addition, it is also possible to generate random libraries in which each bead carries more than one peptide, by coupling of mixtures of amino acids to the beads, as disclosed by Homik et al., *Reactive Polymers*, 22, 213–220 (1994).

Another methodology is disclosed by Geysen et al., *J. Immunol. Meth.*, 102, 259–274 (1987), which involves the synthesis of peptides on derivatized polystyrene pins which are arranged in such a fashion that they correspond to the arrangement of wells in a 96-well microtiter plate. Individual chemical reactions can be performed in each well, thereby yielding individual peptides on each pin. The pins are typically probed using an enzyme linked immunoassay (ELISA) or radioimmunoassay (RIA), carried out in the microtiter wells, or the peptides may be released from the pins and tested in solution. The mimotope approach of Geysen et al. generates diverse peptides that are probed for activity in situ. The best dipeptide sequence is selected for elongation to diverse tripeptides, the best tripeptide is selected for elongation to a tetrapeptide and so on.

Ideally, chemistries that are amenable to combinatorial library synthesis would have the following characteristics: be polymer-supported to facilitate the resin splitting technique; be assembled in high yield with automatable chemistry; and allow the incorporation of a wide variety of chemical functionalities.

Cyclic peptides are generally recognized as possessing enhanced bioavailability due to increased metabolic stability, as well as a relatively constrained conformation when compared to the same sequence in a linear form. The enhanced metabolic stability should allow diminished doses at longer intervals. The restricted conformation should improve the drug selectivity, thereby potentially preventing side-effects. All of these properties are desirable in conjunction with the quest for new drug candidates.

The generation of libraries of cyclic peptides requires, in addition to any previously stated considerations, that the cyclization reaction be performed in a high yield and with a minimum of additional manipulations. Unfortunately, classical cyclization reactions are highly sequence dependent in terms of the expected yields, making the uniform cyclization of a peptide mixture unreliable.

Recent advances in the cyclization of peptides directly on the solid support have improved the synthetic procedure, and even allowed the automation of cyclization reactions based on known cyclization schemes. In the past, cyclizations were typically performed in solution under conditions of high dilution. Polymer-supported cyclizations can both avoid potential side reactions such as oligomerization and facilitate product purification. For example, on-resin cyclization methods have recently been used to prepare cyclopeptides with bridges formed of thioethers, disulfides, or lactams between two side chains, lactams between the amino terminus and a side chain, and lactams between the amino and carboxy termini (reviewed by Zuckermann, *Current Opinion in Structural Biology*, 3, 580–584 (1993)).

The use of resin-bound cyclic peptides and free cyclic peptides in combinatorial libraries is disclosed in WO 92/00091. However, these cyclic peptides do not contain any conformationally constraining element, and in cases where cyclization is achieved, these peptides may still adopt a number of conformations and suffer many of the same shortcomings as linear peptides.

Cyclic semi-random peptide libraries, which are disclosed in WO 95/01800, are exclusively cyclic penta-peptide and hexa-peptide libraries containing one or more randomized amino acids and a conformationally constraining element in the form of an amino acid residue such as proline which fixes the beta turn angles of the adjacent amino acid residues. The advantages of such conformationally constraining elements is stressed by the inventors of this approach. However, inclusion of such elements via incorporation of a particular amino acid residue into the peptide sequence may have detrimental effects on those residues required for receptor recognition or other biological activity. Furthermore, in WO 95/01800, the cyclization reaction is merely another coupling reaction in which the terminal amino group of the linear peptide is coupled to the terminal carboxy group of the peptide.

Backbone cyclized peptides are generally known, as discussed, for instance, in Gilon et al., *Biopolymers*, 31, 745–750 (1991) and in EPO 564,739 A2 and EPO 564,739 A3. Such compounds have not been used for constructing libraries for screening purposes.

In addition, methods are known for combining amino acids and peptides. U.S. Pat. No. 5,010,175 describes another method of incorporating random amino acids into a peptide. According to that method, a mixture of amino acids is incorporated by coupling a mixture in which the individual amino acids are present in varying proportions depending upon their relative rates of reaction in the coupling, e.g., the amount of amino acid is inversely proportional to its rate of coupling.

SUMMARY OF THE INVENTION

It is an object of this invention to provide backbone-cyclic BPI peptide analogs that are novel and that are suited for screening for bioactive molecules. To this end, the present invention provides backbone-cyclized BPI peptide analogs that contain a peptide sequence having at least one building unit comprising an $N^\alpha$-derivative of an amino acid, with at least one backbone nitrogen in each peptide sequence linked to a side chain of at least one other amino acid in the peptide sequence or to at least one other backbone nitrogen in the peptide sequence by a bridging group comprising a disulfide, amide, thioether, thioester, imine, ether, or alkene bridge to form a backbone-cyclized peptide analog. At least one of the building units is preferably located other than at the end of the peptide sequence, and more preferably, none of the building units is located at the end of the peptide sequence.

According to one aspect of the invention, at least one pair of backbone nitrogens in the peptide sequence is linked together to form a BPI peptide analog having the general formula (I):

Formula (I)

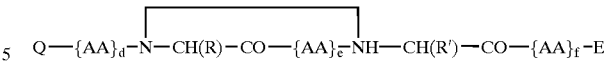

wherein: d, e, and f each independently designates 0 or an integer from 1 to 10; each {AA} designates an amino acid residue or the residue of a plurality of amino acids linked together through peptide bonding, wherein each {AA} may be the same or different; Q represents H or an acyl group; E represents a hydroxyl group, a carboxyl protecting group or an amino group, or the carboxy terminal group CO—E, wherein the CO is part of {AA}, can be reduced to CH$_2$—OH or CHO; each of R and R' is independently hydrogen or an amino acid side-chain optionally bound with a specific protecting group; and the line designates a bridging group of the formula:

(i) —X—M—Y—W—Z—; or (ii) —X—M—Z— wherein: M and W are independently selected from the group consisting of disulfide, amide, thioether, thioester, imine, ether, and alkene; and X, Y and Z are each independently selected from the group consisting of alkylene, substituted alkylene, arylene, homo- or hetero-cycloalkylene and substituted cycloalkylene.

In another aspect of the invention, the backbone of the analog is cyclized to a side-chain of an amino acid to form a peptide analog of the general formula (II):

Formula (II)

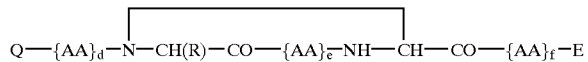

wherein the variables are as disclosed above.

A further backbone-cyclized bicyclic BPI peptide analog includes an $N^\alpha$-derivative of an amino acid and has formula (III):

Formula (III)

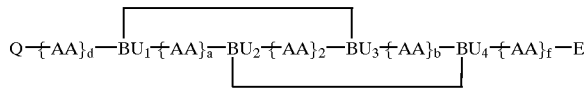

wherein each BU represents an $N^\alpha\omega$-functionalized derivative of amino acids of formula (IV):

Formula (IV)

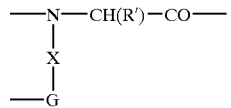

wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; and the other variables are as disclosed above. The BU groups are incorporated into the peptide sequence and may subsequently be selectively cyclized via the functional group G with one of the side chains of the amino acids in said peptide sequence or with another ω-functionalized amino acid derivative.

It is preferred that libraries of these peptide analogs be prepared for screening to determine biologically active compounds. In accordance with the present invention, these libraries have at least four members. In a preferred embodiment, the library as described above comprises two or more sublibraries, each containing a plurality of related peptide analogs.

The present invention also provides methods for the preparation of these peptide analogs and to libraries of such analogs. The methods comprise the steps of providing peptide sequences having a plurality of building units containing amino acids and linked nitrogen atoms and incorporating into each peptide sequence at least one $N^\alpha\omega$-functionalized derivative of an amino acid of formula (IV) by selectively cyclizing a functional group G with another $\omega$-functionalized amino acid derivative or with one of the side chains of the amino acids in said peptide sequence to form backbone-cyclized BPI peptide analogs.

Preferred embodiments for G in formula (IV) include amine, thiol, and carboxyl groups. Preferred embodiments for R and R' in formulas (I)–(III) include $CH_3$—, $(CH_3)_2CH$—, $(CH_3)_2CHCH_2$—, $CH_3CH_2CH(CH_3)$—, $CH_3S(CH_2)_2$—, $HOCH_2$—, $CH_3CH(OH)$—, $HSCH_2$—, $NH_2C(=O)CH_2$—, $NH_2C(=O)(CH_2)_2$—, $NH_2(CH_2)_3$—, $HOC(=O)CH_2$—, $HOC(=O)(CH_2)_2$—, $NH_2(CH_2)_4$—, $C(NH_2)_2 NH(CH_2)_3$—, HO-phenyl-$CH_2$—, benzyl, methylindole, and methylimidazole.

A particularly useful embodiment of the present invention involves providing the BPI peptide analogs as described above covalently coupled to insoluble polymeric supports.

The present invention likewise provides a method of screening compounds which comprises forming a library of backbone cyclized BPI peptide analogs as described herein and screening the analogs for BPI activity.

DESCRIPTION OF THE PREFERRED EMBODIMENTS

In order to fully describe the present invention, the following definitions will be used:

A "library" of backbone cyclized BPI peptide analogs indicates a collection of BPI peptide analogs wherein at least one conformational constraint consisting of a bridge linking novel building units via modified side chains attached to the nitrogens of the amide bonds is present. Typically the amino acids in other positions of the peptide will be "variable" or "constant". Each library is characterized by its building units, its constant amino acid residues and its variable amino acid residues. Each library may be composed of "sub-libraries" which are synthesized in parallel, using a divergent or convergent synthetic scheme.

A "variable" position or amino acid residue may have more than one amino acid in the specified position of the peptide. Typically, in a set of sub-libraries, each sub-library differs from the other in the identity of at least one of its defined amino acid(s) (e.g., the defined amino acid(s) will be constant throughout a single sub-library, yet differ between sub-libraries within the set). A "constant" amino acid or sequence is one whose identity and position are invariant throughout the peptides of the library, and across a set of sub-libraries.

The conformation of a peptide backbone is determined by the three dihedral angles $\phi(C$-$N$-$C\alpha$-$C)$, $\psi(N$-$C\alpha$-$C$-$N)$ and $\omega(C\alpha$-$C$-$N$-$C\alpha)$, which not only specify the position of the peptide backbone atoms, but also the angle of projection of the amino acid side chains (Ca-Cb vector) from the peptide backbone. A peptide with a "conformationally constrained backbone" will either be rigid, existing in only a single conformer characterized by specific values of $\phi$, $\psi$, and $\omega$ for each residue, or will exist as an equilibrium mixture of a relatively few discrete conformers, the backbone torsional angles of all residues for each conformer being well described. Thus, a backbone-cyclic peptide with a conformational constraint indicates one in which the atoms and bonds which constitute the ring are energetically able to assume only a limited number of positions in space relative to one another at or around room temperature, and these positions may be well defined by conventional techniques of molecular modeling and crystallography.

An "optimized" conformer is that which has the greatest activity (e.g., biological response, binding or inhibition of biological response or binding) when a library having a defined amino acid sequence is screened for a given target activity. Preferably, only a single bridge will confer optimal activity. An optimized bridge is characterized by its chemical structure and position in the peptide sequence The "amino acid set" comprises all amino acids which are to be varied within the peptide at a particular position. Typically the amino acid set will comprise 2–50 different amino acid residues. The amino acid set may be varied in the number of amino acid residues and types of residues for each position in the peptide, or the same set may by used for all positions in the peptide.

The term "amino acid" refers to compounds which have an amino terminus and carboxy terminus, preferably in a 1,2- 1,3-, or 1,4-substitution pattern on a carbon backbone. $\alpha$-Amino acids are most preferred, and include the 20 natural amino acids (which are L-amino acids except for glycine), which are found in proteins, the corresponding D-amino acids, the biosynthetically available amino acids which are not found in proteins (e.g., 4-hydroxy-proline, 5-hydroxy-lysine, citrulline, ornithine, canavanine, djenkolic acid, $\beta$-cyanolanine), and synthetically derived $\alpha$-amino acids, such as amino-isobutyric acid, norleucine, norvaline, homocysteine and homoserine. $\beta$-Alanine and $\gamma$-aminobutyric acid are examples of 1,3- and 1,4-amino acids, and many others are well known to the art. Statine-like isosteres (a dipeptide comprising two amino acids wherein the CONH linkage is replaced by a CHOH), hydroxyethylene isosteres (a dipeptide comprising two amino acids wherein the CONH linkage is replaced by a $CHOHCH_2$), reduced amide isosteres (a dipeptide comprising two amino acids wherein the CONH linkage is replaced by a $CH_2NH$ linkage) and thioamide isosteres (a dipeptide comprising two amino acids wherein the CONH linkage is replaced by a CSNH linkage) are also useful residues for this invention.

As used herein "peptide" indicates a sequence of amino acids linked by peptide bonds. The peptide analogs of this invention comprise a sequence of amino acids of 4 to 12 amino acid residues, preferably 6 to 10 residues, each residue being characterized by having an amino and a carboxy terminus.

A "building unit" indicates an $N^\alpha$-derivatized $\alpha$-amino acid of the general Formula (IV):

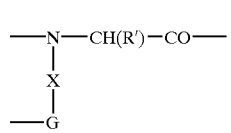

Formula (IV)

wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; which is incorporated into the peptide sequence and subsequently selectively cyclized via the functional group G with one of the side chains of the amino acids in said peptide sequence or with another w-functionalized amino acid derivative.

The methodology for producing the building units is described in U.S. Pat. No. 5,874,529, which is expressly incorporated herein by reference thereto. The building units are abbreviated by the three letter code of the corresponding modified amino acid followed by the type of reactive group (N for amine, C for carboxyl), and an indication of the number of spacing methylene groups. For example, Gly-C2 describes a modified Gly residue with a carboxyl reactive group and two methylene spacer, and Phe-N3 designates a modified phenylalanine group with a amino reactive group and three methylene spacer.

As used herein "linear peptide" denotes the peptide sequence that is constructed only of amino acid residues and is devoid of any building units.

As used herein "backbone cyclic peptide" denotes an analog of a linear peptide which contains at least one building unit that has been linked to form a bridge via the alpha nitrogen of the peptide backbone to another building unit, or to another amino acid in the sequence.

As used herein "pre-cyclic peptide" denotes an analog identical to the cyclic analog except that it is retained in the non-cyclized form to serve as control during the biological or other screening assays.

"Pre-cyclic peptide library" denotes the portion of the peptide analog library, containing the building units identical to those of the backbone cyclized library, but is devoid of the conformational constraint of the latter.

Certain abbreviations are used herein to describe this invention and the manner of making and using it. For instance, AcOH refers to acetic acid, Ada refers to adamantanacetyl, Adac refers to adamantanecarbonyl, Alloc refer to allyloxycarbonyl, BCIP refers to 5-bromo-4-chloro-3-indolyl phosphate, Boc refers to the t-butyloxycarbonyl radical, BOP refers to benzotriazol-1-yloxy-tris-(dimethylamino)phosphonium hexafluorophosphate, BPI refers to Bactericidal/permeability increasing protein, BSA refers to bovine serum albumin, Cbz refers to the carbobenzyloxy radical, DCC refers to dicyclohexylcarbodiimide, DCM refers to Dichloromethane, Dde refers to 1-(4,4-dimethyl2,6-dioxocyclohex-1-ylidene-ethyl, DIEA refers to diisopropyl-ethyl amine, DMF refers to dimethyl formamide, DPPA refers to diphenylphosphoryl azide, Dtc refers to 5,5-dimethylthiazolidine-4-carboxylic acid, EDC refers to N-ethyl-N'(dimethylaminopropyl)-carbodiimide, EDT refers to ethanedithiol, Fmoc refers to the fluorenylmethoxycarbonyl radical, HATU refers to [O-(7-azabenzotriazol-1-yl)-1,1,3,3-tetramethyl uronium hexafluorophosphate, HBTU refers to 1-hydroxybenztriazolyltetramethyl-uronium hexafluorophosphate, HF refers to hydrofluoric acid, HOBT refers to 1-hydroxybenzotriazole, HPLC refers to high pressure liquid chromatography, MALDI-TOF MS refers to matrix-assisted laser desorption, time-of-flight mass spectrometry, Mts refers to the 4-methoxy-2,3,6-trimethylbenzenzsulfonyl, NBT refers to nitro blue tetrazolium, NMM refers to N-methylmorpholine, NMP refers to 1-methyl-2-pyrolidonone, PBS refers to Phosphate buffered saline, Pmc refers to pentamethylchroman-6-sulfonyl, PNPP refers to p-nitrophenyl phosphate, PPA refers to 1-propanephosphoric acid cyclic anhydride, PyBOP refers to Benzotriazole-1-yl-oxy-tris-pyrrolidino-phosphonium hexafluorophosphate, PyBrOP refers to Bromo-tris-pyrrolidino-phosphonium hexafluorophosphate, RT refers to room temperature, SMPS refers to simultaneous multiple peptide synthesis, TBTU refers to 2-(1H-benzotriazole-1-yl)-1,1,3,3-tetramethyluronium tetrafluoroborate, t-Bu refers to the tertiary butyl radical, TFA refers to trifluoroacetic acid, TIS refers to triisopropylsilane, Tpr refers to thiazolidine-4-carboxylic acid, Trt refers to trityl, Ts refers to toluenesulfonyl.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation. List of Non-coded amino acids: Abu refers to 2-aminobutyric acid, Aib refers to 2-amino-isobutyric acid, Cha refers to cyclohexylalanine, Hcys refer to homocysteine, Hyp refers to S-trans-4-hydroxyproline, 1Nal refers to 1-naphtylalanine, 2Nal refers to 2-naphtylalanine, Nva refers to norvaline, Oic refers to octahydroindolecarboxylic acid, Phg refers to phenylglycine, pClPhe refers to p-chloro-phenylalanine, pFPhe refers to p-fluoro-phenylalanine, pNO2Phe refers to p-nitro-phenylalanine, Thi refers to thienylalanine.

According to the present invention, the principles of cyclic peptide libraries have now been successfully applied to the generation of novel mixtures of peptidomimetic compounds, which are characterized in that they incorporate novel building units with modified side chains attached to the alpha nitrogens of alpha amino acids. These novel building units permit the generation of BPI peptidomimetics that are backbone-to-backbone cyclized and conformationally constrained.

The most striking advantages of this approach are:
1) The method enables cyclization of the peptide sequence without compromising the side chains of the peptide sequence that are involved in biological recognition and functionality.
2) The method allows optimization of the peptide conformation by allowing permutation of the bridge length, direction, and bond type (e.g., amide, disulfide, thioether, thioester, etc.) and position of the bond in the ring. 3) When applied to cyclization of linear peptides of known activity, the bridge is expected not to be involved in target recognition, thereby creating a site suitable for attachment of tags such as radioactive tracers, cytotoxic drugs, light capturing substances, or any other desired label.

The peptides of the invention can be collected and placed in libraries to enable screening for varying degrees of conformational constraint, in order to find the optimal backbone conformation of the peptide in performing its role as an agonist or antagonist. This is accomplished by varying both the position of the bridgeheads (i.e., the positions in the linear sequence of residues that are to be cyclized), as well as varying the length, the direction and the bond type of the bridge between these units.

The general methodology for preparing the cyclic peptides of this invention involves solid phase peptide synthesis using an orthogonal protection scheme which allows for chain elongation, selective removal of the protecting groups, cyclization of the protected peptides and removal of all side-chains protecting groups with or without cleavage from the resin. It is desirable that the various peptide sequences be present in the libraries in substantially equal amount.

The coupling reactions are performed by methods to create amide or ester bonds and are performed by methods familiar in the art as described herein. Typical coupling reagents are carbodiimides, activated anhydrides and esters and acyl halides. Reagents such as EDC, DCC, DPPA, PPA, BOP, PyBOP, PyBrop, HATU, HBTU, TBTU, HOBT, N-hydroxysuccinimide and oxalyl chloride are typical.

Synthesis of peptide libraries containing more than one building unit, bridge type or amino acid at one or more positions can be performed by different synthetic schemes, as known in the art of peptide synthesis. Preferred methods of generating libraries include the following:

Partitioning, Coupling, and Recombination Scheme
1. The resin is partitioned into a number of aliquots corresponding to the number of amino acids or building units used for the defined set used at each position.
2. Each aliquot is coupled exhaustively to a single building unit or amino acid using solid phase methodologies.
3. The synthesis subsequently proceeds by recombining of all resin portions before the next coupling step is performed.
4. Steps 1 and 2 may be repeated as necessary, depending on whether a constant or variable residue is being coupled.

Alternatively, in a divergent synthetic scheme, at any given point in the synthesis each resin aliquot may be treated individually from that point on until the end of the synthesis, thus generating sub-libraries. The synthesis may be carried out in parallel for part or all of the remaining synthetic process, up to and including the cyclization and cleavage steps.

Coupling of Mixtures

Synthesis is performed using a mixture of amino acids that are coupled in a certain position to one resin aliquot. The use of exactly one equivalent of total amino acid and the long coupling time serves partially to correct for the different rates of coupling of the individual amino acids in the mixture and to help ensure that an equimolar mixture of amino acids is obtained at each position. The procedure of U.S. Pat. No. 5,010,175 can also be used.

After completion of the solid phase peptide elongation, by any scheme, portions of the peptide are cyclized, via the bridging groups attached to the backbone amide bond nitrogens of the building units. It is preferable that a portion is retained in the non-cyclized form to serve as control during the biological or other screening assays. This portion of the peptide analog library, which contains the building units identical to those of the backbone cyclized library, but is devoid of the conformational constraint of the latter, is referred to as the "pre-cyclic". Alternatively, in any of the synthesis schemes, the backbone cyclization step may be performed and additional coupling cycles of amino acid residues may then be carried out.

Portions of the peptide may be cleaved from the resin and protecting groups removed, as required prior to assay of biological activity. The peptides are cleaved from the resin support by methods known in the art, the precise method being dependent upon the characteristics of the resin. It will be understood by those skilled in the art that the removal of certain protecting groups may occur simultaneously with cleavage of the peptide from the resin.

Typically the coupling between the resin and the first amino acid will form an ester bond, which will yield a carboxylic acid group on the peptide when it is cleaved from the resin. HMPB, Rink, PAM, Hycram and hydroxymethyl resins are exemplary. In addition, the carboxy terminal amino acid group may be converted to an amide, an ester or reduced to a terminal alcohol.

The reactive functional groups of the side chains of each amino acid or peptide are suitably protected as known in the peptide art. For example, the Boc, Cbz or Fmoc group may be used for protection of an amino group, especially an α-amino group. An alkyl (e.g., t-Bu, Me), cHex, benzyl or allyl ester may be used for the protection of the side chain carboxyl of Asp or Glu. A benzyl, or suitably substituted benzyl, trityl, Alloc or t-Bu group is used to protect the mercapto group of cysteine, or other thiol containing residues; or the hydroxyl of Tyr, Ser or Thr, Cys and other sulfur-containing amino acids may also be protected by the Acm group or by formation of a disulfide with a thioalkyl (e.g., ethyl mercaptan) or thioaryl group. The benzyl/benzyloxymethyl, or a suitably substituted benzyl/benzyloxymethyl, Boc or formyl group may be used for protection of the imidazolyl group of His; and the Pmc, nitro or a suitably substituted benzene-sulfonyl group (e.g., Ts, Mts) for protection of the guanidino nitrogen of Arg. The phthalamido, Boc, Fmoc, Alloc carbobenzyloxy or benzyl group, or suitably substituted benzyl or benzyloxy group, may be used for protecting the (-amino group of lysine. Suitable substitution of the carbobenzyloxy or benzyl protecting groups is substitution with one to five chloro, bromo, nitro, methoxy or methyl groups, usually ortho and/or para, and is used to modify the reactivity of the protective group. These protective groups are removed by such methods as catalytic hydrogenation, sodium in liquid ammonia, hydrazine, base, TFA or HF treatment, as known in the art. The choice of side chain protecting groups is chosen so that they will not be removed under conditions which are used to deprotect the reactive functional group used in the coupling reaction (e.g., generally the (-amino group) to form the peptide backbone of the peptide chain. The protective group of the reactive functional group is removed prior to coupling each successive amino acid.

The bridging groups of the building units (i.e., G in Formula IV) are used according to the present invention with an orthogonal protection scheme, such that these protecting groups can be removed selectively, under conditions which do not affect the protecting groups on the side chains or cleavage of the peptide from the resin. This enables backbone cyclization on the resin, which is preferred synthetically. Alternatively, the fully protected peptide may be removed from the resin, and cyclization performed in solution after selective removal of the protecting groups of the building units.

The cyclization reaction is carried out by means of selective coupling the bridging group of one building unit to a bridging group of another building unit or amino acid side chain. By way of example, the PyBOP is particularly useful reagent for conducting the coupling reaction, in case of formation of an amide bond. To form a disulfide bridge oxidative conditions are used.

A typical scheme for preparing libraries according to the invention involves using resin such as TentaGel or Rink resin as the support, Fmoc as the (-amino protecting group, t-butyl based protecting groups for the side chains, and allyl/Alloc for the side chain of building unit. Other schemes of orthogonal protection known to those skilled in the art are obviously applicable as well. Generally, one will calculate the number of amino acids in the amino acid set for each position in the peptide, and will use sufficient resin so that there is at least a five-fold molecular excess of reactive sites on the resin to the number of possible peptide sequences.

When the C-terminal amino acid is variable, it is convenient to begin the synthesis using a mixture of individual aminoacyl peptide resins with an equimolar distribution of the amino acids used. An equimolar mixture of the same protected amino acids can also be prepared. An aliquot of the protected amino acid mixture corresponding to exactly one equivalent of total amino acid is allowed to couple to the resin mixture. The use of exactly one equivalent of total amino acid and the long coupling time serves partially to correct for the different rates of coupling of the individual amino acids in the mixture and to help ensure that an equimolar mixture of amino acids is obtained at each position. At this point, a Kaiser test may be performed to assess the completeness of coupling and recoupling with one equivalent of the equimolar mixture can be performed as necessary.

The amino acid sequence scaffold is based on known active sequences from BPI protein. It will thus be possible to further improve the activity of such known sequences, such as by rigidification of the active conformer.

The application of the present invention is particularly suitable for peptides of 3 up to 14 amino acid residues. However, it is also useful to define peptide fragments that compete with larger polypeptides having up to 45 to 70 residues. These methods can be used to produce both conformationally constrained agonists and antagonists. They can either optimize the properties of known sequences or generate novel analogs.

Amino acids in certain positions are replaced by Backbone-Cyclization Building-Units or by natural and non-natural trifunctional amino acids such as Asp, Glu, Cys, Hcys, Lys, Orn and their D counterparts. Thus positional as well as structural scans are performed by changing the position of cyclization, the link of the ring to the backbone, the chirality at the position of cyclization, the ring forming bond, the ring size and the exact placement of the bond within the ring. These variations may also be performed in conjunction with changing the amino acids sequence of the peptide.

In one preferred embodiment of the present invention, backbone-cyclic BPI peptide libraries were prepared by Simultaneous Multiple Peptide Synthesis (SMPS, Houghten, *Proc. Natl. Acad. Sci. USA,* 82, 5131–5135, 1985). Resin portions were kept separate by capturing them in polypropylene bags, and coupling and deprotection cycles were performed on all bags together in a polypropylene box, except for steps of coupling of different amino acids at the same sites of the peptides. In each bag there was only one (crude) compound by the end of the synthesis.

After completion of the synthesis, samples of resin-peptide were taken form each bag to make mixtures based on structural homology (e.g. a mixture could be comprised of all peptides with a D-amino acid at a certain position or all peptides with the same ring size etc.). The peptides were cleaved from the resin and screened for biological activity as crude mixtures. Then peptides from the most active mixtures were cleaved separately from the resin, purified by preparative HPLC, characterized by mass-spectrometry and amino-acid-analysis and assayed for their biological activity.

Backbone-cyclic peptides containing a disulfide bond in the ring were prepared by inclusion of protected ω-thiol building units in the sequence. Backbone to backbone cyclization was performed by disulfide bond formation between two such building units in a given sequence. Alternatively were backbone to side-chain cyclic peptides prepared by closing a disulfide ring between the w-thiol group of a building unit and the thiol group of Cys or HCys. Formation of the disulfide bond on the resin was obtained by adaptation of the diphenylsulfoxide-silyl chloride method (Akaji et. al., *J. Amer. Chem. Soc.,* 114, 4137, 1992). This is done as was presented in the literature (Camarero et. al., *Tetrahedron Lett.,* 36, 1137–1140, 1995) for prolonged periods (16–24 h) at room temperature. The yields were not high but were sufficient for biological screening. A backbone-bicyclic peptide library was prepared by combining lactam and disulfide cyclizations. Analogs of [Arg6]SP6–11 where Met11 was replaced by an w-thiol containing building unit, Cys or HCys, and Gly9 was replaced by an w-amine building unit were synthesized manually in SMPS bags using Fmoc chemistry. The w-amino group of the building unit in position 9 was protected by Boc. After coupling of this building unit the Boc group was removed and to the w-amine was coupled a second w-thiol building unit or amino acid with its a-amine protected with Boc. Then the Fmoc group was removed from the a-amine of the building unit in position 9 and the synthesis of the peptides was continued. After completion of the synthesis of the hexapeptide chain, a dicarboxylic acid was coupled to the amino terminus and then the Boc group protecting the α-amino group of the ω-thiol containing building unit or amino acid was removed and the lactam ring was closed. Then the disulfide ring was closed by the above mentioned solid-phase diphenylsulfoxide-silyl chloride method. Since the yields of these peptides were relatively low due to side-reactions in the disulfide formation step, the peptides comprising the most active mixtures were re-synthesized and cyclized separately after cleavage from the resin by the normal solution diphenylsulfoxide-silyl chloride method.

In another preferred embodiment, libraries are synthesized by the portioning-mixing method (Furka et al., *Int. J. Pep. Protein Res.,* 37, 487–493, 1991). Typically, in each variable position the resin is split into the appropriate number of aliquots, and different amino acids or building units are coupled to each. Any appropriate reaction vessel may be used to contain these aliquots; in a preferred embodiment it is very convenient to use an individual column for each portion of the resin. After the coupling is completed and the coupling mixture is washed out, all or part of the resin portions are recombined. Removal of α-N protecting groups (typically Fmoc) is performed on the re-combined resin. Further cycles of coupling, and the other steps, are carried out similarly with or without portioning and mixing of the resin. Preferably, in this scheme of production, the library consists of several sub-libraries which differ in one or more amino acid residue, building unit and/or bridge. The final resin portions (sub-libraries) are cyclized to yield backbone cyclized mixtures or left as pre-cyclic mixtures. After removal of side-chain protecting groups and optional cleavage of the sub-library peptides from the resin, screening of the sub-libraries set leads to identification of an optimized sub-library. Further synthesis and screening cycles lead to the optimized backbone cyclized peptide. In each successive synthetic cycles, the complexity of the mixture is smaller.

In another preferred embodiment libraries are synthesized on non-cleavable resins to yield solid-phase supported libraries. Diversity of bridges and amino acids sequence is achieved by the positional scanning method (reviewed by Pinilla et. al. ibid.).

EXAMPLES

Conformationally constrained peptidomimetic libraries have been constructed based on the sequences of a number of known biologically active peptides. The following peptides serve as examples that are intended to illustrate how to make and use the libraries and methods of this invention and are in no way to be construed as a limitation.

The libraries were synthesized on TentaGel amide Resin (substitution level of 0.2–0.3 mmol/g) using conventional solid-phase peptide synthesis (known to those skilled in the art). In most cased NMP was used as a solvent, DMF in few cases. Synthesis scale was 0.2–2 (mole for each peptide in library or sub-library. Unless mentioned, all reactions were performed at room temperature.

In each coupling step where more then one amino acid had to be coupled, the resin was divided into the appropriate number of portions and different amino acid was added to each portion.

Coupling was performed, twice for each position with 3 molar excess of each amino acid, 3 molar excess of PyBrop and 6 molar excess of DIEA for duration of 1–16 hours. All amino acids were protected with FMOC in their (-amine. Side-chain protections were as follow: His(Trt); Lys(Boc or Dde); Orn(Boc); Ser(tBu); Thr(tBu); Tyr(tBu).

After double coupling, the resin portions were washed, recombined and FMOC deprotection was performed using 20% piperidine in NMP for total of 20–40 minutes. After additional washes the resin was divided again (if necessary) for the coupling of the next amino acid/s.

Before cyclization, the Allyl/Alloc protection of the amine and carboxyl of the building units were removed by treatment with a solution of 2 mole equivalents (one for each Allyl/Alloc molecule in peptide), of Pd(PPh3)4 dissolved in chloroform containing 2.5% AcOH and 5% NMM for 2–2.5 hours or twice for 1 hour, resins were washed with the above solvent without the palladium before and after treatment, additional washes with NMP were made at the end of the removal process.

For cases were the backbone-cyclic library and the pre-cyclic libraries are synthesized simultaneously, the resin was divided into separate portions before cyclization and cyclization was performed only for the "cyclic library" portion. The corresponding linear library was synthesized separately because it contains non-modified amino acids instead of the building units. Cyclization was performed twice or three times, each with 3 molar excess of PyBOP and 6 molar excess of DIEA for 2–16 hours with NMP washes between and after coupling.

The peptides were cleaved from the resin portions after washes with DCM, by double treatment with TFA 70%, H2O 5%, TIS 1%, EDT 2.5%, DCM (mixture A) or TFA 70%, H2O 5%, TIS 1%, Phenol 5%, DCM (mixture B) or 60% TFA, 10% H2O and 30% DCM (mixture C) plus additional wash with neat TFA. The three cleavage solutions of each resin portion were collected together, evaporated with nitrogen stream, 0.5–1 ml of H2O were added to each sample that was then freeze-dried. The peptide mixtures were then partially purified on C-18 SEP-PAK (Millipore Corp.) using 0.1% acetic acid or TFA in H2O as buffer A and 50–80% CH3CN in 0.1% acetic acid/H20 as buffer B and freeze-dried.

Yields of semi-purified peptide mixtures were generally 10–60% of initial synthesis scale. Optimization of synthetic procedures during scale-up will lead to higher yields. Each sub-library synthesized was characterized by mass spectrometry (MALDI-TOF MS), and amino acid analysis.

The building units are abbreviated by the three letter code of the corresponding modified amino acid followed by the type of reactive group (N for amine, C for carboxyl), and an indication of the number of spacing methylene groups. For example, Gly-C2 describes a modified Gly residue with a carboxyl reactive group and two methylene spacer, and Phe-N3 designates a modified phenylalanine group with a amino reactive group and three methylene spacer.

BPI libraries synthesized according to these schemes were tested for their inhibition of fungi growth. Libraries were also tested for their stability to enzymatic degradation by incubation in serum or in tissue homogenate, separation of the proteins and recording of the peptide peaks by HPLC before and after incubation. The peptide peaks that are not changed with increased incubation time are most stable for degradation. These peaks are separated and characterized by mass spectrometry, N-terminal sequence and comparison to purified peptide peaks. In this way the most stable peptides from library or sub-library are rapidly identified.

BPI Peptides $BPI_{23}$ is an amino terminal recombinant fragment of the natural 55-KDa cationic protein bactericidal/permeability increasing protein (BPI, Little et. al. 1994, J.Biol.Chem. 269:1865–1872). The $BPI_{23}$ fragment has all the antibacterial and antiendotoxin properties of the holoprotein against Gram-negative bacteria. Epitope mapping of the active fragment yielded a 15 amino acids bactericidal peptide. Later, another domain was found to have anti-fungal activity. The 10-mer linear peptide: Lys-Trp-Leu-Ile-Gln-Leu-Phe-His-Lys-Lys-NH ((SEQ. ID NO: 1) amino acids 152–161 in the $BPI_{23}$ sequence), served as our basic sequence for producing backbone-cyclic peptide libraries in the aim of developing anti-fungal peptidomimetic drugs with higher potency, less toxicity and longer half-life than linear peptides.

Usually, for identifying the amino acids critical for activity and those that might be replaced (by building units in our case), one would perform an "Alanine scan" substituting each amino acid in the sequence by Alanine and testing the influence on the peptide activity. Because of the fact that no information was available on the conformation and the structure-activity-relationship of the basic active linear deca-peptide we decided to define the optimal cyclization points within the linear sequence directly by synthesis of backbone-cyclic peptide libraries.

The first BPI library that was synthesized (IG-BPI1), contained various cyclization points between positions 153–160 (because of synthetic and rational reasons, the Lys residues of positions 152 and 160 were not substituted). The goal was to determine whether a particular bridge position is favored and which amino acids in the linear sequence can not be substitute. The backbone-cyclic, the pre-cyclic and the linear (actually a double "Glycine scan"), libraries were synthesized and tested. The anti-fungal results, indicate that the activity was preserved to a significant extend in the cyclic peptides. Overall, pre-cyclic peptides were less active than either the corresponding backbone cyclic peptides or linear peptides. Sub-library A6 in which the backbone cyclic peptides were more active than the linear, was the most interesting sub-library, although the differences between the four backbone cyclic sub-libraries were not large. The information obtained from the backbone-cyclic library with additional information from separate backbone-cyclic analogs, served as basis for the design of the next BPI backbone-cyclic libraries.

The BPI libraries were tested for their anti Candida albicans activity in an in-vitro radial diffusion assay. Briefly, candida are incorporated into agarose and a series of wells are punched into the solidified agarose. A small volume of each library/sub-library sample (serially diluted) is placed into each well and allowed to diffuse into the agarose. An overlayer is then poured over the plate and the assay is incubated overnight. Fungicidal zones are measured with a micrometer for each sample dilution. The amount of peptide added to the well that create a net 30 mm2 zone gives the recorded activity result. For a given sample to create a radial diffusion zone, the candida must be killed, therefore this assay distinguish between fungicidal and fungistatic compounds.

In order to validate positive signals of the anti-fungal tests, and to eliminate non-specific signals, library samples of somatostatin-peptides that were synthesized and handled in the same procedures and assume to contain the same contaminants, were tested in the same assays as negative control samples. These samples had no activity in any of the anti-fungal assays.

In addition, the sub-library samples are tested in the radial diffusion assay after incubation in human serum for testing the metabolic stability of these samples and comparison between the stability of backbone-cyclic vs pre-cyclic and linear libraries.

Peptides were anchored to the beads by a linker that is cleavable by natural pH treatment (Salmon et. al., *Proc. Natl. Acad. Sci.*, 90, 11708–11712, 1993), the beads are placed in agarose as for radial diffusion assay and the peptides are cleaved to the surrounded media and will inhibit the fungi growth.

The peptides were synthesized on non-cleavable linker, the beads are placed as above into the agarose and the peptides will inhibit the growth of the fungi or bacteria by binding to essential factors (enzymes etc.) in the media, or cell membrane components.

Table I summarizes some of the libraries of BPI that were synthesized and characterized. Position numbers of amino acids in the BPI peptides are based on the sequence of the native $BPI_{23}$ protein.

Example 1

IG-BPI1 Library

This library was synthesized with the aim of finding the best position of the bridge in the basic linear deca-peptide. In each of positions 153–160 either a native amino acid or a building unit (Gly-C2 in positions 153, 154, 155 or 156 and Gly-N2 in positions 157, 158, 159 or 160) was coupled, yielding four sub-libraries including four peptides in each. The sub-libraries differ between them in the position of the Gly-C2 unit, while peptides in each sub-library differ in the position of the Gly-N2 unit. The linear library contain non-modified Gly instead of the building units thus, serve as indication for the necessity of the linear peptide's side-chain groups for activity. The synthesis is illustrated in the following scheme.

As can be seen from the anti-fungal activity results, the backbone-cyclic peptides have improved activity over the pre-cyclic peptides. In one case, sub-library A6, the activity of the backbone-cyclic peptides is even better than the linear sequence.

TABLE I

The composition of several BPI libraries

| Library Name | Library Type | Sequence per position | | | | | | | | | |
|---|---|---|---|---|---|---|---|---|---|---|---|
| | | 152 | 153 | 154 | 155 | 156 | 157 | 158 | 159 | 160 | 161 |
| IG-BPI1 | backbone-cyclic | Lys | Trp<br>Gly-C2 | Leu<br>Gly-C2 | Ile<br>Gly-C2 | Gln<br>Gly-C2 | Leu<br>Gly-N2 | Phe<br>Gly-N2 | His<br>Gly-N2 | Lys<br>Gly-N2 | Lys |
| | pre-cyclic | Lys | Trp<br>Gly-C2 | Leu<br>Gly-C2 | Ile<br>Gly-C2 | Gln<br>Gly-C2 | Leu<br>Gly-N2 | Phe<br>Gly-N2 | His<br>Gly-N2 | Lys<br>Gly-N2 | Lys |
| | linear | Lys | Trp<br>Gly | Leu<br>Gly | Ile<br>Gly | Gln<br>Gly | Leu<br>Gly | Phe<br>Gly | His<br>Gly | Lys<br>Gly | Lys |
| IG-BPI3 | backbone-cyclic | Lys | Trp | Leu | Ile<br>Gly<br>Ala<br>none | Gly-C2 | Leu | Phe<br>DPhe<br>Phg<br>pNO2Phe<br>pFPhe | His | Gly-N2 | Lys |
| | pre-cyclic | Lys | Trp | Leu | Ile<br>Gly<br>Ala<br>Des | Gly-C2 | Leu | Phe<br>DPhe<br>Phg<br>pNO2Phe<br>pFPhe | His | Gly-N2 | Lys |
| IG-BPI4 | backbone-cyclic | Lys | 2Nal<br>D2Nal<br>1Nal<br>D1Nal | Gly-C1<br>Gly-C2<br>Gly-N2<br>Gly-N3 | Ile | Gln | Leu | Phe | Gly-N2<br>Gly-N3<br>Gly-C1<br>Gly-C2 | Lys | Lys |
| | pre-cyclic | Lys | 2Nal<br>D2Nal<br>1Nal<br>D1Nal | Gly-C1<br>Gly-C2<br>Gly-N2<br>Gly-N3 | Ile | Gln | Leu | Phe | Gly-N2<br>Gly-N3<br>Gly-C1<br>Gly-C2 | Lys | Lys |

All peptides have an amide C-terminal

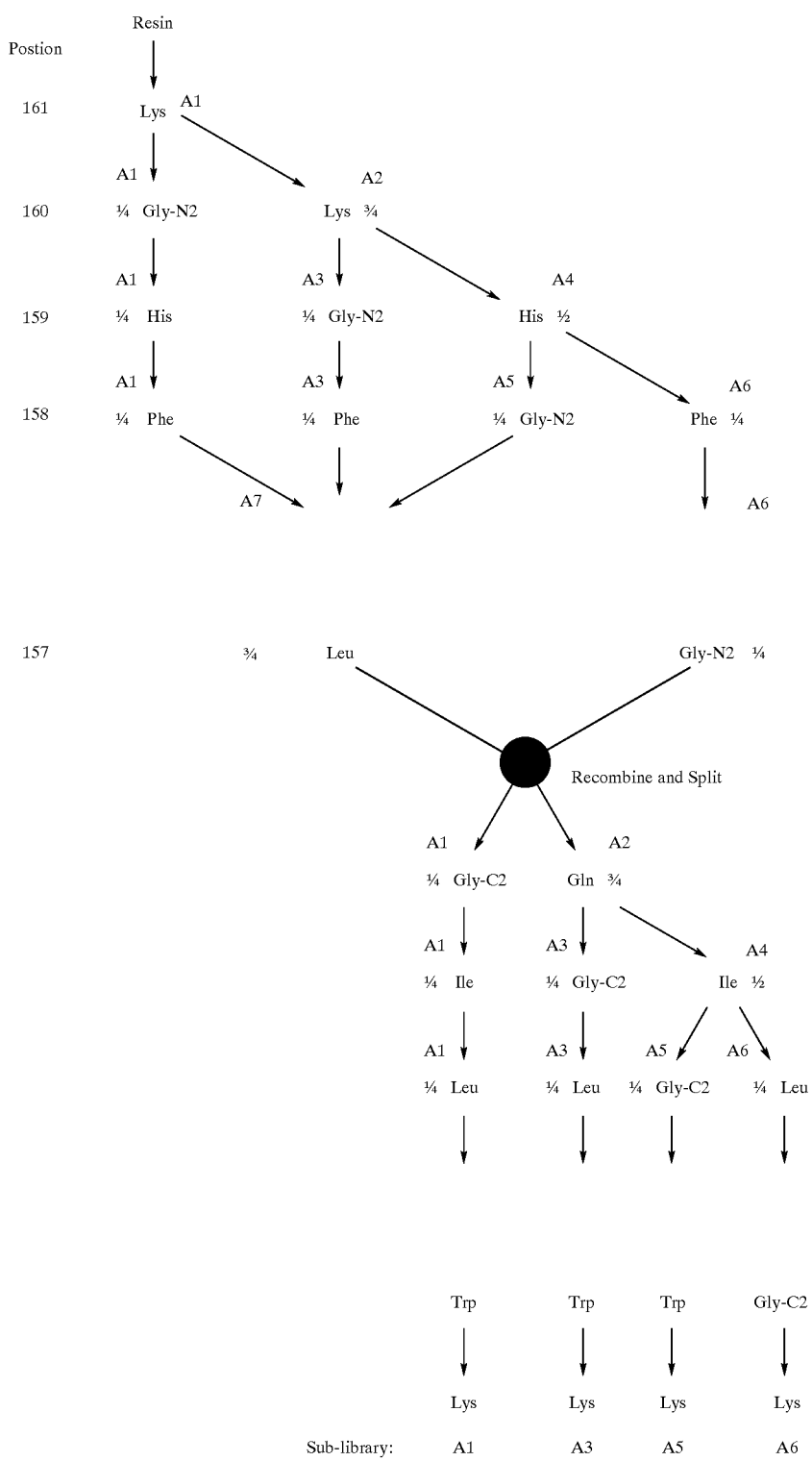

Example 2

IG-BPI3 Library

The synthesis scheme of this library containing total of 20 peptides in 4 sub-libraries is described in the following scheme. One of the sub-libraries (A) contains nona-peptides instead of deca-peptides. This was done in order to test the importance of the Ile residue at position 155 (amino acid indicated as "Des" in the composition table), for activity and to check wherever it is possible to substitute or preferably, delete it from the original sequence. The backbone-cyclic and the pre-cyclic libraries were synthesized simultaneously.

The sub-libraries were tested for their anti-fungal activity in the radial diffusion assay and the results are summarized in table II.

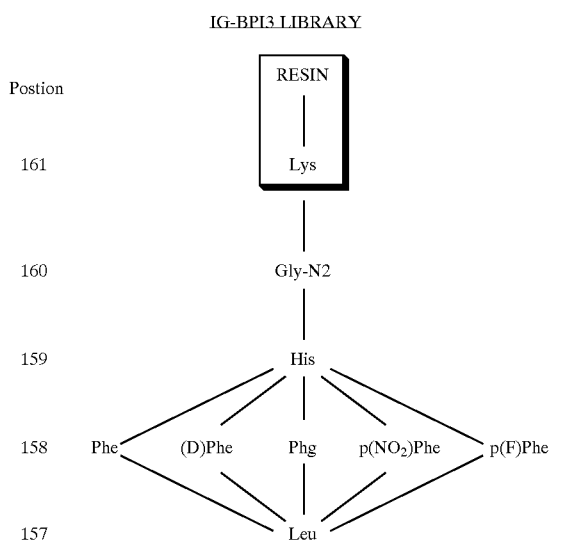

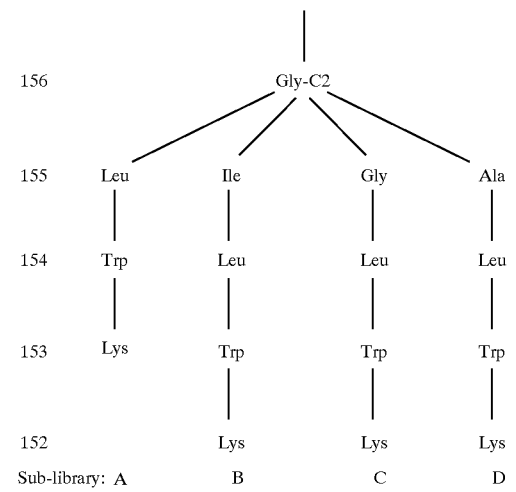

TABLE II

Composition and anti-fungal activity of IG-BPII1 library.

| Sub-library | Peptide sequence — Position | | | | | | | | | | Seq ID No. | Amount needed for anti-fungal activity[1] | | |
|---|---|---|---|---|---|---|---|---|---|---|---|---|---|---|
| | 152 | 153 | 154 | 155 | 156 | 157 | 158 | 159 | 160 | 161 | | Backbone cyclic | Pre-cyclic | Linear |
| A1 | Lys | Trp | Leu | Ile | Gly-C2 | Leu | Phe | His | Gly-N2 | Lys | SEQ ID NO:2 | 12.2 | 27.0 | 2.1 |
| | Lys | Trp | Leu | Ile | Gly-C2 | Leu | Phe | Gly-N2 | Lys | Lys | SEQ ID NO:3 | | | |
| | Lys | Trp | Leu | Ile | Gly-C2 | Leu | Gly-N2 | His | Lys | Lys | SEQ ID NO:4 | | | |
| | Lys | Trp | Leu | Ile | Gly-C2 | Gly-N2 | Phe | His | Lys | Lys | SEQ ID NO:5 | | | |
| A3 | Lys | Trp | Leu | Gly-C2 | Gln | Leu | Phe | His | Gly-N2 | Lys | SEQ ID NO:6 | 17.4 | 36.2 | 7.47 |
| | Lys | Trp | Leu | Gly-C2 | Gln | Leu | Phe | Gly-N2 | Lys | Lys | SEQ ID NO:7 | | | |
| | Lys | Trp | Leu | Gly-C2 | Gln | Leu | Gly-N2 | His | Lys | Lys | SEQ ID NO:8 | | | |
| | Lys | Trp | Leu | Gly-C2 | Gln | Gly-N2 | Phe | His | Lys | Lys | SEQ ID NO:9 | | | |
| A5 | Lys | Trp | Gly-C2 | Ile | Gln | Leu | Phe | His | Gly-N2 | Lys | SEQ ID NO:10 | 30.4 | 44.6 | 18.1 |
| | Lys | Trp | Gly-C2 | Ile | Gln | Leu | Phe | Gly-N2 | Lys | Lys | SEQ ID NO:11 | | | |
| | Lys | Trp | Gly-C2 | Ile | Gln | Leu | Gly-N2 | His | Lys | Lys | SEQ ID NO:12 | | | |
| | Lys | Trp | Gly-C2 | Ile | Gln | Gly-N2 | Phe | His | Lys | Lys | SEQ ID NO:13 | | | |
| A6 | Lys | Gly-C2 | Leu | Ile | Gln | Leu | Phe | His | Gly-N2 | Lys | SEQ ID NO:14 | 8.9 | 65.5 | 17.5 |
| | Lys | Gly-C2 | Leu | Ile | Gln | Leu | Phe | Gly-N2 | Lys | Lys | SEQ ID NO:15 | | | |
| | Lys | Gly-C2 | Leu | Ile | Gln | Leu | Gly-N2 | His | Lys | Lys | SEQ ID NO:16 | | | |
| | Lys | Gly-C2 | Leu | Ile | Gln | Leu | Phe | His | Lys | Lys | SEQ ID NO:17 | | | |

[1] The amount of peptide sample (in μg) added to the well to create a net 30 mm² fungal-inhibition zone.

Example 3

IG-BPI4 Library

The composition of this library, as illustrated in the following scheme was based on an active peptide (synthesized and tested separately) with the sequence: Lys-D1Nal-[Gly-C2-Ile-Gln-Lue-Phe-Gly-N2]-Lys-Lys-NH2 (SEQ. ID NO:18). With the aim of finding the best bridge size and orientation, four different building units (Gly-C1, Gly-C2, Gly-N2 and Gly-N3), were used for cyclization between positions 154 and 159. Simultaneously, the influence of different Naphtylalanine (Nal) residues at position 153 was also evaluated. The 4 sub-libraries differ in their residue at position 153 and the peptides (total 32) in each sub-libraries differ in their bridge type or size. For rapid identification of the preferred bridging building unit at position 154, portions from each of the four peptide-resins (with positions 161–154), after coupling of the building units, were removed before recombination and kept. After identification of the active sub-library (by the anti-fungal assay), the "best" Naphtylalanine residue will be coupled to each of the 4 resin portions. After coupling of Lys to each (position 152) portion, the new 4 sub-libraries were tested for activity.

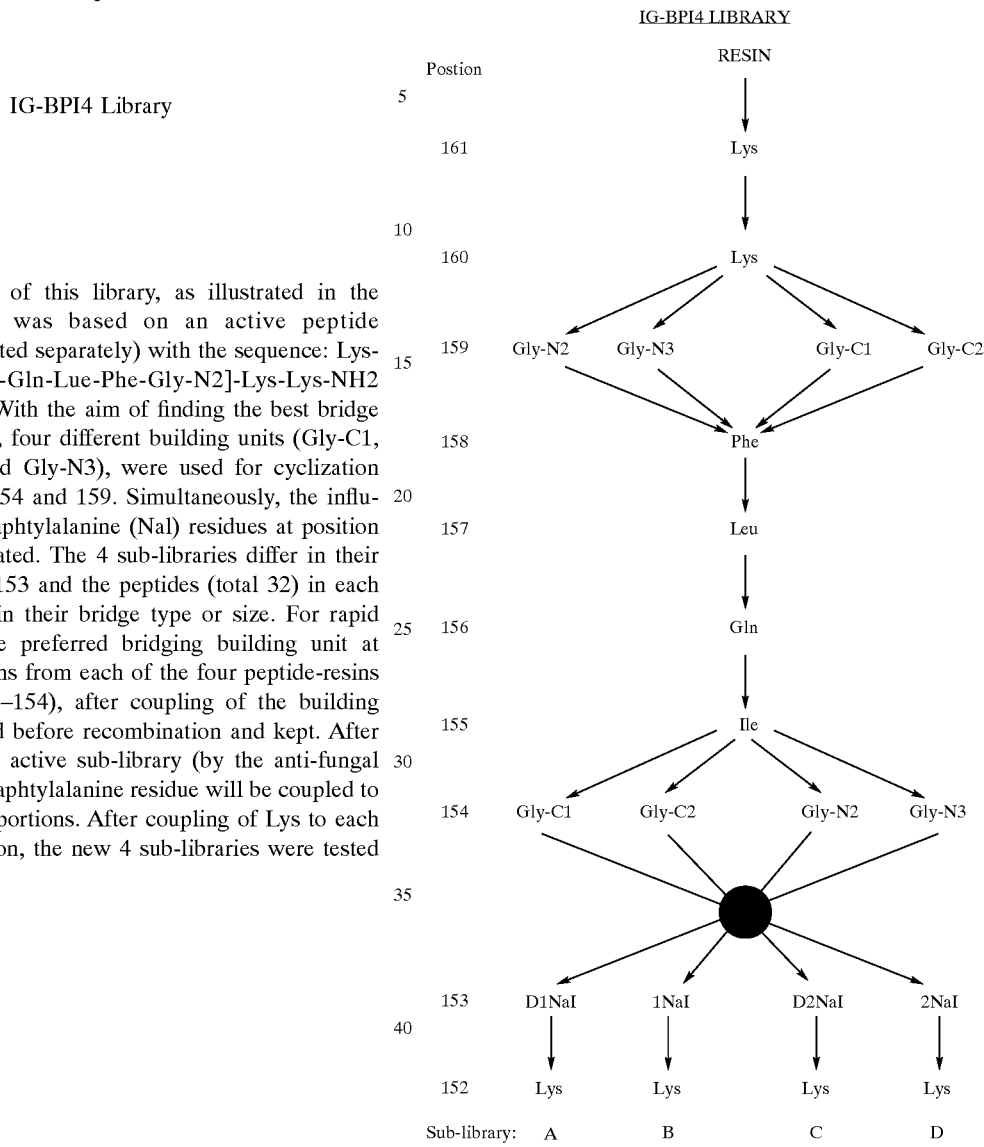

What is claimed is:

1. A backbone-cyclized peptidomimetic of a fragment of bacterial/permeability increasing protein 23 (BPI$_{23}$) having anti-fungal activity comprising the following BPI$_{23}$ peptide sequence:

(SEQ ID NO:1)
Q-Lys-Trp-Leu-Ile-Gln-Leu-Phe-His-Lys-Lys-E
   152            156            161 wherein: Q represents H or an acyl group; E represents a hydroxyl group, a carboxyl protecting group or an amino group, or the carboxy terminal group CO—E, wherein the CO is part of an amino acid residue, can be reduced to CH$_2$—OH or CHO and wherein up to four amino acid residues of the BPI$_{23}$ peptide sequence, amino acid residues 153–160, are replaced with a building unit, a different amino acid residue or is absent and wherein the BPI$_{23}$ peptide sequence has at least one building unit with at least one backbone nitrogen in the peptide sequence linked to a side chain of at least one other amino acid in the peptide sequence or to at least one other backbone nitrogen in the peptide sequence by a bridging group comprising a disulfide, amide, thioether, thioester, imine, ether, or alkene to form a backbone-cyclized peptidomimetic having anti-fungal activity.

2. The peptidomimetic of claim 1, wherein at least two building units are incorporated in the BPI$_{23}$ peptide sequence.

3. The peptidomimetic of claim 1, wherein at least one pair of backbone nitrogens in the BPI$_{23}$ peptide sequence are linked together.

4. The peptidomimetic of claim 1, wherein the bridging group has the formula:

(i) —X—M—Y—W—Z—; or (ii) —X—M—Z— wherein: M and W are independently selected from the group consisting of disulfide, amide, thioether, thioester, imine, ether, and alkene; and X, Y and Z are each independently selected from the group consisting of alkylene, substituted alkylene, arylene, homo- or hetero-cycloalkylene and substituted cycloalkylene.

5. The peptidomimetic of claim 4 wherein —X—M—Y—W—Z— is: —(CH$_2$)$_x$—M—(CH$_2$)$_y$—W—(CH$_2$)$_2$— wherein M and W are as recited above; x and z each independently designates an integer of from 1 to 10, and y is zero or an integer of 1 to 8, with the proviso that if y is zero, W is absent.

6. The peptidomimetic of claim 1, wherein at least one backbone nitrogen is cyclized to a side-chain of an amino acid.

7. The peptidomimetic of claim 1, wherein the building unit is an N$^\alpha$-ω-functionalized derivative of amino acids of formula (IV):

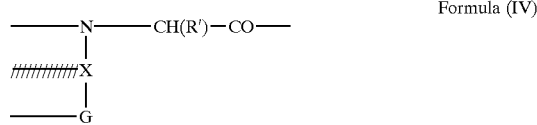

Formula (IV)

wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides, wherein the building unit is incorporated into BPI$_{23}$ peptide sequence and cyclized via the functional group G with one of the side chains of the amino acids in said peptide sequence or with another ω-functionalized amino acid derivative.

8. A backbone-cyclized peptidomimetic of a fragment of bacterial/permeability increasing protein 23 comprising a peptide sequence having at least one building unit having an N$^\alpha$-derivative of an amino acid, wherein at least one backbone nitrogen in the peptide sequence is linked to a side chain of at least one other amino acid in the peptide sequence or to at least one other backbone nitrogen in the peptide sequence by a bridging group comprising a disulfide, amide, thioether, thioester, imine, ether, or alkene to form a backbone-cyclized peptidomimetic, wherein the peptide sequence has the formula:

Q-Lys-AA$_2$-AA$_3$-AA$_4$-AA$_5$-AA$_6$-AA$_7$-AA$_8$-AA-$_9$-Lys-E wherein: Q represents H or an acyl group; E represents a hydroxyl group, a carboxyl protecting group or an amino group, or the carboxy terminal group CO—E, wherein the CO is part of an amino acid residue, can be reduced to CH$_2$—OH or CHO; AA$_2$ is Trp, 2Nal, D2Nal, 1Nal, D1Nal, Gly-C*, or Gly-N*; AA$_3$ is Leu, Gly-C* or Gly-N*; AA$_4$ is absent, Ile, Gly Ala, Gly-C* or Gly-N*; AA$_5$ is Gln, Gly-C* or Gly-N*; AA$_0$ is Leu, Gly-C* or Gly-N*; AA$_7$ is Phe, DPhe, Phg, pNO2Phe, pFPhe, Gly-C* or Gly-N*; AA$_8$ is His, Gly-C* or Gly-N*; AA$_9$ is Lys, Gly-C* or Gly-N*; and * is an integer from 1 to 3, wherein a bridging group extends from one of AA$_2$, AA$_3$, or AA$_5$ to one of AA$_6$, AA$_7$, AA$_8$, or AA$_9$ to form a cyclic structure having anti-fungal activity.

9. The backbone-cyclized peptidomimetic of claim 8, wherein AA$_2$ is Trp or Gly-C2; AA$_3$ is Leu or Gly-C2; AA$_4$ is Ile or Gly-C2; AA$_5$ is Gln or Gly-C2; AA$_6$ is Leu or Gly-N2; AA₇ is Phe or Gly-N2; AA₈ is His or Gly-N2; and AA₉ is Lys or Gly-N2.

10. The backbone-cyclized peptidomimetic of claim 9, wherein AA₂ is Gly-C2; AA₃ is Leu; AA₄ is Ile; and AA₅ is Gln.

11. The backbone-cyclized peptidomimetic of claim 9, wherein AA₂ is Gly-C2; AA₃ is Leu; AA₄ is Ile; and AA₅ is Gln; AA₆ is Leu; AA₇ is Phe; AA₈ is Gly-N2; and AA₉ is Lys.

12. The backbone-cyclized peptidomimetic of claim 8, wherein AA₁ is Lys; AA₂ is Trp; AA₃ is Leu; AA₄ is Ile, Gly or Ala; AA₅ is Gly-C2; AA₆ is Leu; AA₇ is Phe, DPhe, Phg, pNO2Phe, or pFPhe; AA₈ is His; and AA₉ is Gly-N2.

13. The backbone-cyclized peptidomimetic of claim 8, wherein AA₁ is Lys; AA₂ is 2Nal, D2Nal, 1Nal, or D1Nal; AA₃ is Gly-C1, Gly-C2, Gly-N2 or Gly-N3; AA₄ is Ile; AA₅ is Gln; AA₆ is Leu; AA₇ is Phe; AA₈ is Gly-C1, Gly-C2, Gly-N2 or Gly-N3; and AA₉ is Lys, wherein if AA₃ is Gly-C1 or Gly-C2, AA₈ is Gly-N2 or Gly-N3, and if AA₃ is Gly-N2 or Gly-N3, AA₈ is Gly-C1 or Gly-C2.

14. The backbone-cyclized peptidomimetic of claim 13, wherein AA₂ is 1Nal.

* * * * *

UNITED STATES PATENT AND TRADEMARK OFFICE
CERTIFICATE OF CORRECTION

PATENT NO.     : 6,706,862 B1
DATED          : March 16, 2004
INVENTOR(S)    : Hornik Page 1 of 1

It is certified that error appears in the above-identified patent and that said Letters Patent is hereby corrected as shown below:

<u>Title page,</u>
After Item [62], Related U.S. Application Data, insert the following:
-- [30] Foreign Application Priority Data
Aug. 29, 1995 (IL) ………………….. 115096 --.
Item [56], References Cited, FOREIGN PATENT DOCUMENTS, change
"WO     0 564 739 A2 *   10/1993" to -- EP     0 564 739 A2 *   10/1993 --.
Item [57], ABSTRACT,
Line 6, change "$N^\alpha$-functionalized amino acids" to
-- $N^\alpha$-$\omega$-functionalized amino acids --; and line 11, change "Na$\omega$-functionalized amino acids" to -- $N^\alpha$-$\omega$-functionalized amino acids --.

<u>Column 33,</u>
Line 60, change "—$(CH_2)_x$ — M— $(CH_2)_y$—W—$(CH_2)_2$—" to
-- —$(CH_2)_x$—M—$(CH_2)_y$—W—$(CH_2)_z$— --.
Line 63, after "is zero or an integer of" insert -- from --.

<u>Column 34,</u>
Line 50, after "Q—Lys—$AA_2$—$AA_3$—$AA_4$—$AA_5$—$AA_6$—$AA_7$—$AA_8$—$AA_9$—Lys—E" insert -- (SEQ ID NO: 19) --.
Line 59, change "or Gly-N*; $AA_0$ is Leu,Gly-C* or Gly-N*"; to -- Gly-N*; $AA_6$ is Leu, Gly-C* or Gly-N* --.
Line 63, after "from one of $AA_2$, $AA_3$" insert -- $AA_4$, --.

Signed and Sealed this

Twenty-ninth Day of June, 2004

JON W. DUDAS
*Acting Director of the United States Patent and Trademark Office*